United States Patent
Pillai

(10) Patent No.: US 7,048,705 B2
(45) Date of Patent: May 23, 2006

(54) TRACTION ADJUSTABLE CERVICAL COLLAR FOR TRANSFERRING WEIGHT OF THE HEAD OF A WEARER FROM THE CERVICAL SPINE OF THE WEARER TO THE SHOULDERS OF THE WEARER

(76) Inventor: Bala Hari Pillai, P.O.Box 121, Laurel, NY (US) 11948-0121

( * ) Notice: Subject to any disclaimer, the term of this patent is extended or adjusted under 35 U.S.C. 154(b) by 0 days.

(21) Appl. No.: 10/890,499

(22) Filed: Jul. 13, 2004

(65) Prior Publication Data

US 2006/0015048 A1    Jan. 19, 2006

(51) Int. Cl.
*A61F 5/00* (2006.01)
(52) U.S. Cl. .......................................... 602/18; 602/13
(58) Field of Classification Search .................. 602/18, 602/13, 17; 128/DIG. 23, 845, 846
See application file for complete search history.

(56) References Cited

U.S. PATENT DOCUMENTS

| | | | | |
|---|---|---|---|---|
| 2,806,471 A | * | 9/1957 | Breese | 602/17 |
| 4,597,384 A | * | 7/1986 | Whitney | 601/152 |
| 5,402,535 A | * | 4/1995 | Green | 2/468 |
| 5,403,266 A | * | 4/1995 | Bragg et al. | 602/5 |
| 5,752,927 A | * | 5/1998 | Rogachevsky | 602/18 |
| 6,050,965 A | * | 4/2000 | Pillai | 602/18 |
| 6,151,735 A | * | 11/2000 | Koby et al. | 5/644 |
| 2003/0158015 A1 | * | 8/2003 | Watson | 482/10 |

* cited by examiner

*Primary Examiner*—Henry Bennett
*Assistant Examiner*—Dinnatia Doster Green

(57) ABSTRACT

A traction adjustable cervical collar transferring weight of the head from the cervical spine to the shoulders. A collar portion releasably encircles the neck and is inflated by inflating apparatus. A bladder of the inflating apparatus is a part of the collar portion and a squeezable hand bulb of the inflating apparatus selectively inflates the bladder. The bladder has a lowermost surface that is flat for preventing slippage along the shoulders of the wearer. The bladder has a pair of side walls and contains a plurality of ribs extending upwardly from the lowermost surface thereof and which have a portion of the pair of side walls of the bladder adjacent thereto being attached thereto so as to provide rigidity to the bladder and prevent it from rolling over onto itself during use.

6 Claims, 2 Drawing Sheets

TRACTION ADJUSTABLE CERVICAL COLLAR FOR TRANSFERRING WEIGHT OF THE HEAD OF A WEARER FROM THE CERVICAL SPINE OF THE WEARER TO THE SHOULDERS OF THE WEARER

BACKGROUND OF THE INVENTION

1. Field of the Invention

The present invention relates to a cervical collar, and more particularly, the present invention relates to a traction adjustable cervical collar for transferring weight of the head of a wearer from the cervical spine of the wearer to the shoulders of the wearer.

2. Description of the Prior Art

About 10% of the adult population suffers from neck pain of some type from time to time. The increased use of computers, travel, and driving, and the increase in sports and other trauma are causing an increase in neck related problems.

Pain may be moderate to severe and may be localized to the neck area or radiate to surrounding tissues. The actual origin of the pain could come from the spinal cord or its roots, the spinal column, the intervertebral discs, or the other support and soft tissue around the neck.

Numerous innovations for cervical orthopaedic devices have been provided in the prior art that will be described. Even though these innovations may be suitable for the specific individual purposes to which they address, however, they differ from the present invention.

FOR EXAMPLE, U.S. Pat. No. 3,765,412 to Ommaya teaches a medical appliance comprising an inflatable cervical collar adapted to be disposed about the neck of the wearer.

ANOTHER EXAMPLE, U.S. Pat. No. 4,805,603 to Cumberland teaches a cervical traction apparatus comprising a head/neck/shoulder support unit having a vertical slot in the region corresponding to the cervical area. The slot separates the unit into a first section and a second section. The upper surfaces of the support unit are shaped to receive the head, neck, and shoulders of a reclining person. An inflatable air sac located within the unit between the first and second sections and provides apparatus for inflating the air sac so as to cause the first and second sections to separate.

STILL ANOTHER EXAMPLE, U.S. Pat. No. 5,027,801 to Grim teaches an orthopaedic gel pad assembly that includes a layer of gel, with a backing layer behind it, an apertured pad extending around the layer of gel, and a thin plastic film extending over the front surface of the gel. The plastic film controls the configuration of the front face of the gel, and the gel may be recessed, or indented, and may protrude forwardly out from the apertured pad. Stiff orthopaedic supports may be provided to back up the gel pad unit.

YET ANOTHER EXAMPLE, U.S. Pat. No. 5,441,479 to Chitwood teaches a cervical traction device which comprises a body including a shoulder portion, a head portion, and a bellows which extends substantially across the width and height of the body between and connected to the head portion and to the shoulder portion and acting against and between substantially the full inner end surface of the head portion and the full inner end surface of the shoulder portion. The bellows, the shoulder portion, and the head portion have aligned U-shaped openings therein adapted to receive a patient's neck. A hand operated air pump is connected to the bellows for pumping air into the bellows and for relieving or pumping air out of the bellows.

STILL YET ANOTHER EXAMPLE, U.S. Pat. No. 5,752,927 to Rogachevsky teaches an inflatable cervical traction device comprising a C-shaped multi-ribbed inflatable hollow collar having four separate chambers. Two of the chambers are located at rear right and left locations of the collar, while the other two chambers are located at front right and left locations of the collar. Structures are for securing two opposite front ends of the collar together in a releasable manner, to hold the collar about a neck of a person. A facility is for pumping air into the four chambers of the collar to inflate each of the four chambers at various pressurized amounts, so that the collar can properly support the neck of the person. An assembly is for releasing air from the four chambers of the collar, so that the collar can deflate to be easily removed from the neck of the person.

YET STILL ANOTHER EXAMPLE, U.S. Pat. No. 6,050,965 to Pillai teaches a cervical collar for lifting the skull of a wearer. The collar includes a core, a pair of bladders, and inflating apparatus. The core replaceably encircles the neck of the wearer. The pair of bladders are inflatable and disposed on the core. The inflating apparatus is in fluid communication with the pair of bladders, and when the pair of bladders are inflated to a predetermined pressure by the inflating apparatus, the skull of the wearer is gently pushed off the shoulders of the wearer, which relieves downward pressure on the cervical spine of the wearer by forming intrinsic neck traction, whose early and continued use relieves pain and weakness and prevents major and sometimes non-reversible deterioration of the cervical spine of the wearer.

STILL YET ANOTHER EXAMPLE, U.S. Pat. No. 6,554,785 to Sroufe teaches an orthopedic device of a therapeutic nature which includes an air bladder and an overlying gel bladder. The air and gel bladders are joined and are secured within a retainer which is adapted to be placed about a body part of a patient with the air or gel bladder being positioned next to the body part.

It is apparent that numerous innovations for cervical orthopaedic devices have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a traction adjustable cervical collar for transferring weight of the head of a wearer from the cervical spine of the wearer to the shoulders of the wearer that avoids the disadvantages of the prior art.

ANOTHER OBJECT of the present invention is to provide a traction adjustable cervical collar for transferring weight of the head of a wearer from the cervical spine of the wearer to the shoulders of the wearer that is simple to use.

STILL ANOTHER OBJECT of the present invention is to provide a traction adjustable cervical collar for transferring weight of the head of a wearer from the cervical spine of the wearer to the shoulders of the wearer that effectively complements chiropractic and manipulative therapy in whiplash injuries, degenerative diseases of the vertebrae and discs, herniated cervical discs, acute and chronic muscular problems, cervical nerve radiculopathy, and mild to severe neck pain from other causes where traction can be beneficial.

YET ANOTHER OBJECT of the present invention is to provide a traction adjustable cervical collar for transferring weight of the head of a wearer from the cervical spine of the wearer to the shoulders of the wearer whose degree of traction can be finely controlled.

STILL YET ANOTHER OBJECT of the present invention is to provide a traction adjustable cervical collar for transferring weight of the head of a wearer from the cervical spine of the wearer to the shoulders of the wearer that is comfortable to wear assuring compliance to treatment regimen.

YET STILL ANOTHER OBJECT of the present invention is to provide a traction adjustable cervical collar for transferring weight of the head of a wearer from the cervical spine of the wearer to the shoulders of the wearer that is easy to keep clean.

STILL YET ANOTHER OBJECT of the present invention is to provide a traction adjustable cervical collar for transferring weight of the head of a wearer from the cervical spine of the wearer to the shoulders of the wearer that allows the wearer to be ambulatory by allowing movement of the head and not interfering with speech.

YET STILL ANOTHER OBJECT of the present invention is to provide a traction adjustable cervical collar for transferring weight of the head of a wearer from the cervical spine of the wearer to the shoulders of the wearer that rests anteriorly on the clavicles and the sternocleidomastoid muscles and posteriorly on the trapezius muscles.

STILL YET ANOTHER OBJECT of the present invention is to provide a traction adjustable cervical collar for transferring weight of the head of a wearer from the cervical spine of the wearer to the shoulders of the wearer that does not impinge upon any of the vital anterior neck organs.

YET STILL ANOTHER OBJECT of the present invention is to provide a traction adjustable cervical collar for transferring weight of the head of a wearer from the cervical spine of the wearer to the shoulders of the wearer that stretches the supporting muscles and structures of the neck and thereby providing true cervical traction so as to allow healing to take place.

BRIEFLY STATED, STILL YET ANOTHER OBJECT of the present invention is to provide a traction adjustable cervical collar transferring weight of the head from the cervical spine to the shoulders. A collar portion releasably encircles the neck and is inflated by inflating apparatus. A bladder of the inflating apparatus is a part of the collar portion and a squeezable hand bulb of the inflating apparatus selectively inflates the bladder. The bladder has a lowermost surface that is flat for preventing slippage along the shoulders of the wearer. The bladder has a pair of side walls and contains a plurality of ribs extending upwardly from the lowermost surface thereof and which have a portion of the pair of side walls of the bladder adjacent thereto being attached thereto so as to provide rigidity to the bladder and prevent it from rolling over onto itself during use.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows.

LIST OF REFERENCE NUMERALS UTILIZED IN THE DRAWING

Figure 1:
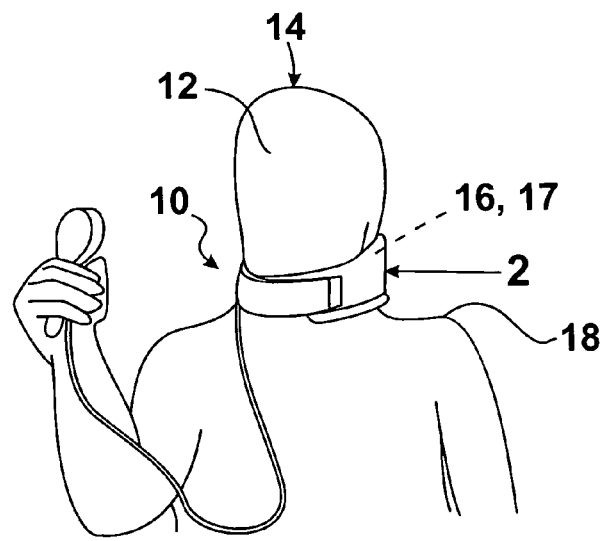
FIG. 1 is a diagrammatic perspective view of the traction adjustable cervical collar of the present invention transferring weight of the head of a wearer from the cervical spine of the wearer to the shoulders of the wearer.

10 traction adjustable cervical collar of present invention for transferring weight of head 12 of wearer 14 from cervical spine 16 of neck 17 of wearer 14 to shoulders 18 of wearer 14.
12 head of wearer 14
14 wearer
16 cervical spine of neck 17 of wearer 14
17 neck of wearer 14
18 shoulders of wearer 14
20 collar portion for releasably encircling neck 17 of wearer 14
22 inflating apparatus
24 squeezable hand bulb of inflating apparatus 22
26 bladder of inflating apparatus 22
28 conduit of inflating apparatus 22
30 first end of conduit 28 of inflating apparatus 22
32 second end of conduit 28 of inflating apparatus 22
34 flexible tube of conduit 28 of inflating apparatus 22
36 manometer of inflating apparatus 22
38 cushion of collar portion 20 for releasably encircling neck 17 of wearer 14
40 lowermost surface of cushion 38 of collar portion 20
42 entire length of lowermost surface 40 of cushion 38 of collar portion 20
44 pair of ends of cushion 38 of collar portion 20
46 pair of ends of bladder 26 of inflating apparatus 22
48 lowermost surface of bladder 26 of inflating apparatus 22
49 pair of side walls of bladder 26 of inflating apparatus 22
50 plurality of ribs in bladder 26

DETAILED DESCRIPTION OF THE INVENTION

Referring now to the figures in which like numerals indicate like parts, and particularly to FIG. 1, which is a diagrammatic perspective view of the traction adjustable cervical collar of the present invention transferring weight of the head of a wearer from the cervical spine of the wearer to the shoulders of the wearer, the traction adjustable cervical collar of the present invention is shown generally at 10 for transferring weight of the head 12 of a wearer 14 from the cervical spine 16 of the neck 17 of the wearer 14 to the shoulders 18 of the wearer 14.

Figure 2:
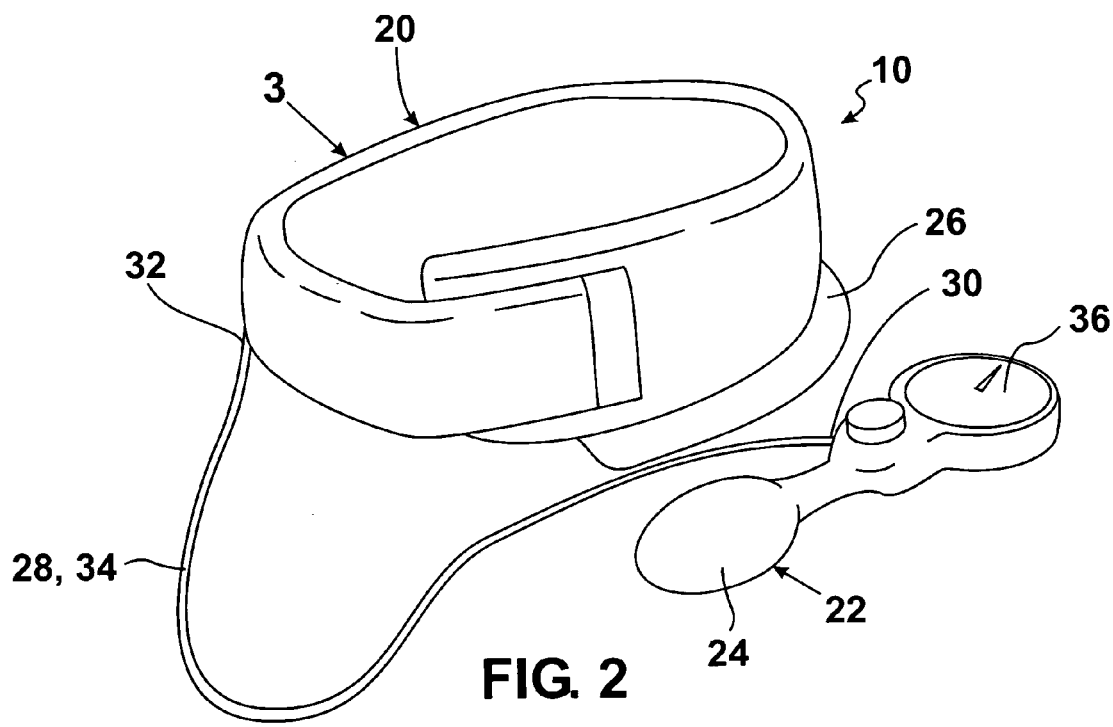
FIG. 2 is an enlarged diagrammatic perspective view of the traction adjustable cervical collar of the present invention identified by ARROW 2 in FIG. 1.

The general configuration of the traction adjustable cervical collar 10 can best be seen in FIG. 2, which is an enlarged diagrammatic perspective view of the traction adjustable cervical collar of the present invention identified by ARROW 2 in FIG. 1, and as such, will be discussed with reference thereto.

The traction adjustable cervical collar 10 comprises a collar portion 20 and inflating apparatus 22. The collar portion 20 is for releasably encircling the neck 17 of the wearer 14 and the inflating apparatus 22 inflates the collar portion 20 for a desired traction and thereby transfers the weight of the head 12 of the wearer 14 from the cervical spine 16 of the wearer 14 to the shoulders 18 of the wearer 14.

The inflating apparatus 22 comprises a squeezable hand bulb 24, a bladder 26, and a conduit 28. The bladder 26 of the inflating apparatus 22 is a part of the collar portion 20, the squeezable hand bulb 24 of the inflating apparatus 22 is remote from, and selectively inflates, the bladder 26 of the inflating apparatus 22, and the conduit 28 of the inflating apparatus 22 fluidly connects the squeezable hand bulb 24 of the inflating apparatus 22 to the bladder 26 of the inflating apparatus 22 so as to allow the squeezable hand bulb 24 of the inflating apparatus 22 to inflate the bladder 26 of the inflating apparatus 22.

The conduit 28 of the inflating apparatus 22 has a first end 30 and a second end 32 and is a flexible tube 34. The first end 32 of the conduit 28 of the inflating apparatus 22 is communicatingly connected to the squeezable hand bulb 24 of the inflating apparatus 22 and the second end 32 of the conduit 28 of the inflating apparatus 22 is communicatingly connected to the bladder 26 of the inflating apparatus 22.

The inflating apparatus 22 further comprises a manometer 36. The manometer 36 of the inflating apparatus 22 is disposed at, and is operatively connected to, the squeezable hand bulb 24 of the inflating apparatus 22 and displays pressure in the bladder 26 of the inflating apparatus 22 so as to allow inflation of the bladder 26 of the inflating apparatus 22 to be finely controlled.

Figure 4:
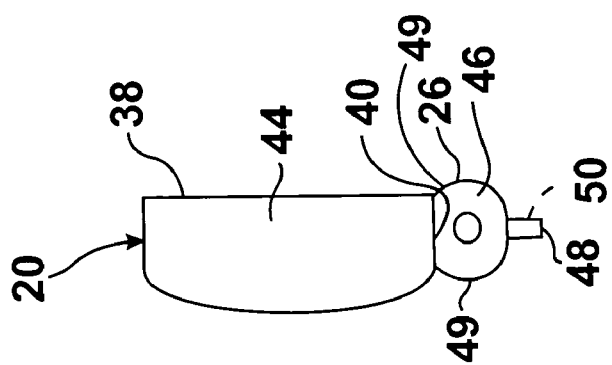
FIG. 4 is a diagrammatic end elevational view taken generally in the direction of ARROW 4 in FIG. 3.
Figure 3:
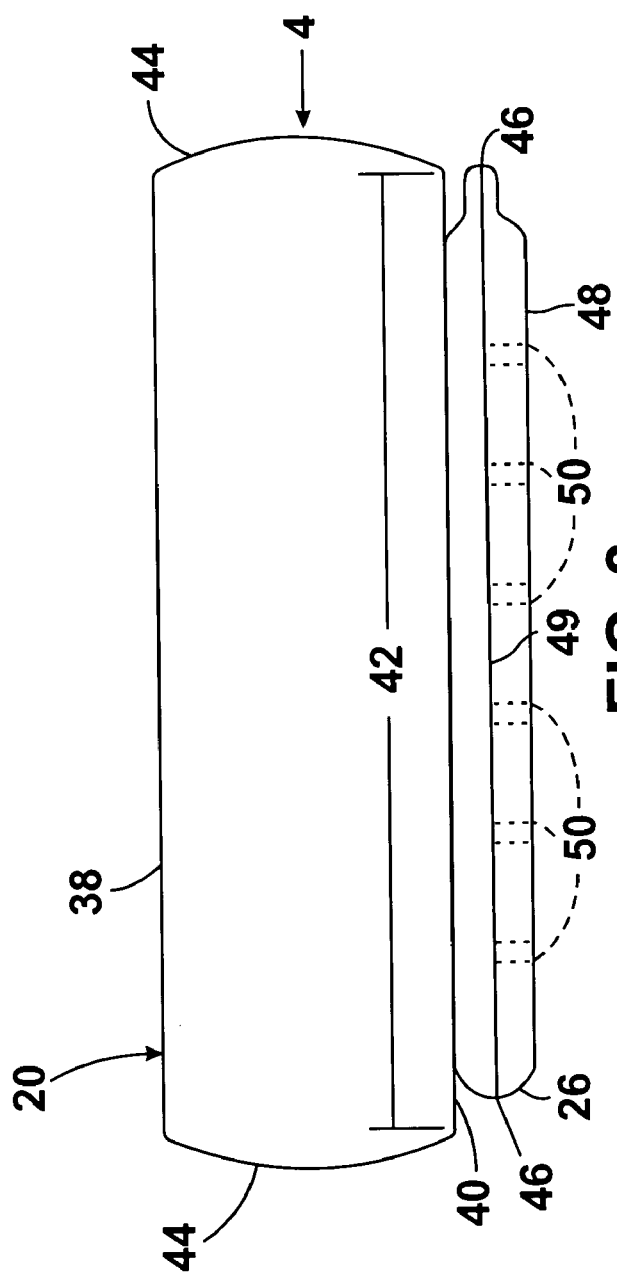
FIG. 3 is an enlarged diagrammatic front elevational view of the collar portion of the traction adjustable cervical collar of the present invention identified by ARROW 3 in FIG. 2.

The specific configuration of the collar portion 20 can best be seen in FIGS. 3 and 4, which is, respectively, an enlarged diagrammatic front elevational view of the collar portion of the traction adjustable cervical collar of the present invention identified by ARROW 3 in FIG. 2 and a diagrammatic end elevational view taken generally in the direction of ARROW 4 in FIG. 3, and as such, will be discussed with reference thereto.

The collar portion 20 comprises a cushion 38 and the bladder 26 of the inflating apparatus 22. The cushion 38 of the collar portion 20 is for releasably encircling the neck 17 of the wearer 14, has a lowermost surface 40 with an entire length 42, a pair of ends 44, and is a gel for comfort to the head 12 and the neck 17 of the wearer 14.

The bladder 26 of the inflating apparatus 22 depends from the lowermost surface 40 of the cushion 38 of the collar portion 20, extends along the entire length 42 of the lowermost surface 40 of the cushion 38 of the collar portion 20, and has a pair of ends 46, a lowermost surface 48, and a pair of side walls 49. The pair of ends 46 of the bladder 26 of the inflating apparatus 22 are in substantial alignment with the pair of ends 44 of the cushion 38 of the collar portion 20.

The bladder 26 of the inflating apparatus 22 is slender and elongated, and the lowermost surface 48 of the bladder 26 of the inflating apparatus 22 is flat for preventing slippage along the shoulders 18 of the wearer 14 so as to rest better thereon. One end 46 of the bladder 26 of the inflating apparatus 22 is communicatingly connected to the second end 32 of the conduit 28 of the inflating apparatus 22.

The bladder 26 of the inflating apparatus 22 contains a plurality of ribs 50. The plurality of ribs 50 in the bladder 26 of the inflating apparatus 22 are spaced-apart from each other, extend upwardly from the lowermost surface 48 of the bladder 26 of the inflating apparatus 22, and have a portion of the pair of side walls 49 of the bladder 26 of the inflating apparatus 22 adjacent thereto being attached thereto so as to provide rigidity to the bladder 26 of the inflating apparatus 22 and prevent it from rolling over onto itself during use.

It will be understood that each of the elements described above, or two or more together, may also find a useful application in other types of constructions differing from the types described above.

While the invention has been illustrated and described as embodied in a traction adjustable cervical collar for transferring weight of the head of a wearer from the cervical spine of the wearer to the shoulders of the wearer, however, it is not limited to the details shown, since it will be understood that various omissions, modifications, substitutions and changes in the forms and details of the assembly illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A traction adjustable cervical collar for transferring weight of the head of a wearer from the cervical spine of the neck of the wearer to the shoulders of the wearer, said collar comprising:
 a) a collar portion; and
 b) inflating apparatus;
 wherein said collar portion is for releasably encircling the neck of the wearer;
 wherein said inflating apparatus inflates said collar portion for a desired traction and thereby transfers the weight of the head of the wearer from the cervical spine of the wearer of the shoulders of the wearer;
 wherein said inflating apparatus comprises a squeezable hand bulb;
 wherein said inflating apparatus comprises a bladder;
 wherein said inflating apparatus comprises a conduit;
 wherein said bladder of said inflating apparatus is a part of said collar portion;
 wherein said squeezable hand bulb of said inflating apparatus is remote from said bladder of said inflating apparatus;
 wherein said squeezable hand bulb of said inflating apparatus selectively inflates said bladder of said inflating apparatus;
 wherein said conduit of said inflating apparatus fluidly connects said squeezable hand bulb of said inflating apparatus to said bladder of said inflating apparatus so as to allow said squeezable hand bulb of said inflating apparatus to inflate said bladder of said inflating apparatus;
 wherein said conduit of said inflating apparatus has a first end;
 wherein said conduit of said inflating apparatus has a second end;
 wherein said first end of said conduit of said inflating apparatus is communicatingly connected to said squeezable hand bulb of said inflating apparatus;
 wherein said second end of said conduit of said inflating apparatus is communicatingly connected to said bladder of said inflating apparatus;
 wherein said collar portion comprises a cushion;
 wherein said collar portion comprises said bladder of said inflating apparatus;

wherein said cushion of said collar portion is for releasably encircling the neck of the wearer;

wherein said cushion of said collar portion has a lowermost surface;

wherein said lowermost surface of said cushion of said collar portion has an entire length;

wherein said cushion of said collar portion has a pair of ends;

wherein said cushion of said collar portion is a gel;

wherein said gel of said cushion of said collar is for comfort to the head and the neck of the wearer; and wherein said bladder of said inflating apparatus depends from said lowermost surface of said cushion of said collar portion;

wherein said bladder of said inflating apparatus extends along said entire length of said lowermost surface of said cushion of said collar portion;

wherein said bladder of said inflating apparatus has a pair of ends;

wherein said pair of ends of said bladder of said inflating apparatus are in substantial alignment with said pair of ends of said cushion of said collar portion;

wherein said bladder of said inflating apparatus has a lowermost surface; and wherein said bladder of said inflating apparatus has a pair of side walls.

2. The collar as defined in claim 1, wherein said conduit of said inflating apparatus is a flexible tube.

3. The collar as defined in claim 1, wherein said inflating apparatus comprises a manometer;

wherein said manometer of said inflating apparatus is disposed at said squeezable hand bulb of said inflating apparatus;

wherein said manometer of said inflating apparatus is operatively connected to said squeezable hand bulb of said inflating apparatus; and wherein said manometer of said inflating apparatus displays pressure in said bladder of said inflating apparatus so as to allow inflation of said bladder of said inflating apparatus to be finely controlled.

4. The collar as defined in claim 1, wherein said bladder of said inflating apparatus is slender;

wherein said bladder of said inflating apparatus is elongated; and wherein said lowermost surface of said bladder of said inflating apparatus is flat for preventing slippage along the shoulders of the wearer so as to rest better thereon.

5. The collar as defined in claim 1, wherein one end of said bladder of said inflating apparatus is communicatingly connected to said second end of said conduit of said inflating apparatus.

6. The collar as defined in claim 4, wherein said bladder of said inflating apparatus contains a plurality of ribs;

wherein said plurality of ribs in said bladder of said inflating apparatus are spaced-apart from each other;

wherein said plurality of ribs in said bladder of said inflating apparatus extend upwardly from said lowermost surface of said bladder of said inflating apparatus;

wherein said plurality of ribs in said bladder of said inflating apparatus have a portion of said pair of side walls of said bladder of said inflating apparatus adjacent thereto being attached to so as to provide rigidity to said bladder of said inflating apparatus and to prevent it from rolling over onto itself during use.

* * * * *